(12) United States Patent
Beck (10) Patent No.: US 9,933,384 B2
(45) Date of Patent: Apr. 3, 2018

(54) CHEMICAL SENSOR SYSTEM

(71) Applicant: Honeywell International Inc., Morris Plains, NJ (US)

(72) Inventor: Scott Edward Beck, Murphy, TX (US)

(73) Assignee: Honeywell International Inc., Morris Plains, NJ (US)

( * ) Notice: Subject to any disclaimer, the term of this patent is extended or adjusted under 35 U.S.C. 154(b) by 35 days.

(21) Appl. No.: 15/028,110

(22) PCT Filed: Oct. 7, 2014

(86) PCT No.: PCT/US2014/059419
§ 371 (c)(1),
(2) Date: Apr. 8, 2016

(87) PCT Pub. No.: WO2015/054195
PCT Pub. Date: Apr. 16, 2015

(65) Prior Publication Data
US 2016/0245771 A1    Aug. 25, 2016

Related U.S. Application Data

(60) Provisional application No. 61/888,290, filed on Oct. 8, 2013.

(51) Int. Cl.
*G01N 27/22* (2006.01)

(52) U.S. Cl.
CPC ......... *G01N 27/223* (2013.01); *G01N 27/226* (2013.01)

(58) Field of Classification Search
CPC ............. G01N 27/223; G01N 33/5436; G01N 27/226; G01R 27/2605; G01R 1/0466
(Continued)

(56) References Cited

U.S. PATENT DOCUMENTS

| | | | |
|---|---|---|---|
| 4,429,343 A | 1/1984 | Freud | |
| 4,564,882 A | 1/1986 | Baxter et al. | |

(Continued)

FOREIGN PATENT DOCUMENTS

| DE | 102009029621 A1 | 3/2011 |
|---|---|---|
| EP | 2306181 A1 | 4/2011 |
| WO | 01/75429 A1 | 10/2001 |

OTHER PUBLICATIONS

International Search Report, PCT/US2014/059419, dated Jan. 22, 2015, 3 pages.

(Continued)

*Primary Examiner* — Melissa Koval
*Assistant Examiner* — Trung Nguyen
(74) *Attorney, Agent, or Firm* — Conley Rose, P.C.

(57) ABSTRACT

An example approach and structure for providing a chemical sensor, having an electrode that may receive a fluid that is passed on towards a dielectric between the electrode and one or more other electrodes. A capacitance between the electrodes may be changed by the dielectric which is affected by a parameter of the fluid. Measuring a change of the capacitance may indicate a magnitude of the parameter. The electrode receiving the fluid may have one or more layers of metal particles that by design of the particles and their arrangement can result in determined pore sizes and routes through the electrode for a controllable porosity of the electrode.

20 Claims, 5 Drawing Sheets

(58) Field of Classification Search
USPC ..... 324/600, 686–693, 702–710, 676, 76.11,
324/76.77, 323, 360, 120
See application file for complete search history.

(56) References Cited

U.S. PATENT DOCUMENTS

| | | | |
|---|---|---|---|
| 6,222,376 B1 | 4/2001 | Tenney, III | |
| 6,724,612 B2 | 4/2004 | Davis et al. | |
| 6,867,602 B2 | 3/2005 | Davis et al. | |
| 7,683,636 B2* | 3/2010 | Alimi .................. | G01N 27/223 324/664 |
| 7,710,128 B2 | 5/2010 | Alimi et al. | |
| 7,924,028 B2 | 4/2011 | Alimi et al. | |
| 2002/0031447 A1* | 3/2002 | Brinz .................. | G01N 21/783 422/88 |
| 2012/0220041 A1 | 8/2012 | Colla et al. | |

OTHER PUBLICATIONS

Walcarius, A., et al., "Ordered porous thin films in electrochemical analysis", Trends in Analytical Chemistry, 2008, pp. 593-603, vol. 27, No. 7, Elsevier Ltd., Amsterdam, NL.

Wen, T., et al., "Ultra-Large-Area Self-Assembled Monolayers of Nanoparticles", ACS NANO, Nov. 22, 2011, pp. 3868-3876, vol. 5, No. 11, published online.

Lohmuller, T., et al., "Nano-porous electrode systems by colloidal lithography for sensitive electrochemical detection: fabrication technology and properties", Journal of Micromechanics & Microengineering, Sep. 26, 2008, 29 pages, vol. 18, No. 11, Institute of Physics Publishing, Bristol, GB.

\* cited by examiner

CHEMICAL SENSOR SYSTEM

CROSS-REFERENCE TO RELATED APPLICATIONS

This application claims priority to the National Stage of International Application No. PCT/US2014/059419 filed on Oct. 7, 2014, and entitled "A CHEMICAL SENSOR SYSTEM," which claims priority to U.S. Provisional Patent Application Ser. No. 61/888,290 entitled "CONTROLLED POROUS METAL DEPOSITION FOR CHEMICAL SENSORS," filed Oct. 8, 2013, both of which are hereby incorporated by reference in their entirety.

BACKGROUND

This disclosure pertains to sensors, and particularly to fluid chemical sensors.

SUMMARY

The disclosure reveals an example approach and structure for providing a chemical sensor, having an electrode that may receive a fluid that is passed on towards a dielectric between the electrode and one or more other electrodes. A capacitance between the electrodes may be changed by the dielectric which is affected by a parameter of the fluid. Measuring a change of the capacitance may indicate a magnitude of the parameter. The electrode receiving the fluid may have one or more layers of metal particles that by design of the particles and their arrangement can result in determined pore sizes and routes through the electrode for a controllable porosity of the electrode.

DESCRIPTION

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

In some instances of the present fluid chemical sensor structure and approaches for making the structure, monodisperse nanospheres and/or microspheres of metals or metal oxides may be used to create a porous layer in a chemical sensor. In some instances, these spheres may range in diameter from one nanometer or less to 2000 microns or more, as desired. While spherical shaped particles may be described in the present example structure and approach, it is contemplated that any suitable shaped particles may be used, including elliptical particles, non-symmetrical particles, or any other suitable particles, and having appropriate sizes as desired. Microspheres of metals (such as gold, platinum, palladium, silver, chrome, and aluminum) and metal oxides (e.g., titania, and so forth) may be available from companies such as Polysciences, Inc. of Warrington, Pa., and Cabot Corporation of Boston, Mass.

Solid-state chemical sensors may have a porous layer of metal or metal oxide. Depending on the application, this layer may serve as a sensing layer or as an electrode. In the case where the porous layer serves as a sensing layer, the fluid to be sensed may react with the exposed surface of the porous layer. In the case where the porous layer serves as art electrode, the fluid to be sensed should permeate through the pores to reach a sensing material below.

The porous layer might be deposited or formed using a deposition process using a vacuum deposition equipment, or other approach. For instance, in a humidity sensor, a platinum layer that has a desired thickness (e.g., 50 angstroms (Å) as determined electrically) may be provided using a sputter tool that is vacuum based. However, in such cases, the average thickness of the film may be the primary parameter that is directly controllable. There a desire to also control the porosity (e.g., density of pores and/or pore size) and/or pore distribution in the resulting porous layer that may be achieved with the present approach and structure.

Figure 1:
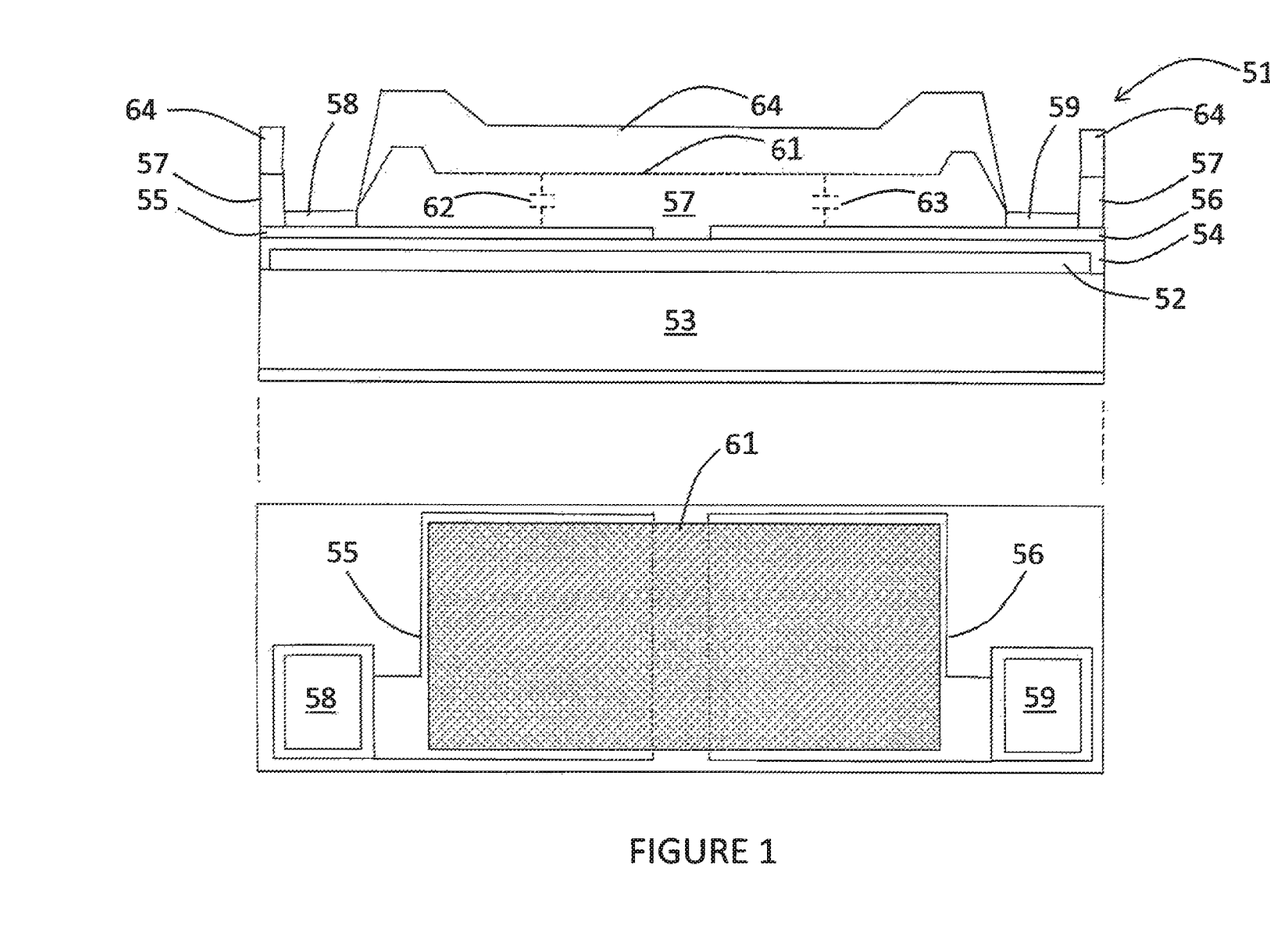
FIG. 1 is a diagram of an illustrative example implementation of a chemical sensor.

FIG. 1 is a diagram of an illustrative example implementation of the present chemical sensor 51. The sensor may be fabricated with various deposition and etching processes. The diagram reveals top and cross section views. A layer of silicon dioxide 52 may be formed on a silicon substrate 53. An electrode buffer layer 54 may be formed on silicon dioxide 52. Then a first TiW electrode 55 and second TW electrode 56 and gold contacts may be formed on layer 54. A dielectric layer 57 of a polyimide may be formed on electrodes 55 and 56. Layer 57 may be etched to expose gold contacts or pads 58 and 59 for connection to electrodes 55 and 56, respectively. A landing or an area at the middle of layer 57 may be formed or etched for placement or deposition of a third electrode 61. Electrode 61 may be situated over electrodes 55 and 56 to form capacitances 62 and 63, between electrode 61 and electrodes 55 and 56, respectively. Electrode 61 may be formed from one or more layers of spherical or other shaped metal particles. Electrode 61 may have pores so that a fluid may make contact with dielectric layer 57. Examples of electrode 61 are described herein. A passivation layer 64 may be formed on sensor 51 and etched or made so as to make pads 58 and 59 accessible for electrical connections to electrodes 55 and 56. Layer 64 may be for protection of sensor 51 but permit breathing of a fluid to electrode 61 and dielectric layer 57. The materials identified for the diagram of sensor 51 are merely examples but may be other kinds of materials as appropriate for making the present chemical sensor. The chemical sensor may have other configurations incorporating more or less electrodes and layers, and have a different structure using other kinds of fabrication technologies and techniques. The electrodes or plates of a capacitor of the sensor may have an interdigital finger-like design with an intermesh of the electrodes. Many other electrode designs may be utilized in the present sensor. Also, the sensor may have components that are more or less discrete with various arrangements of them.

Figure 2:
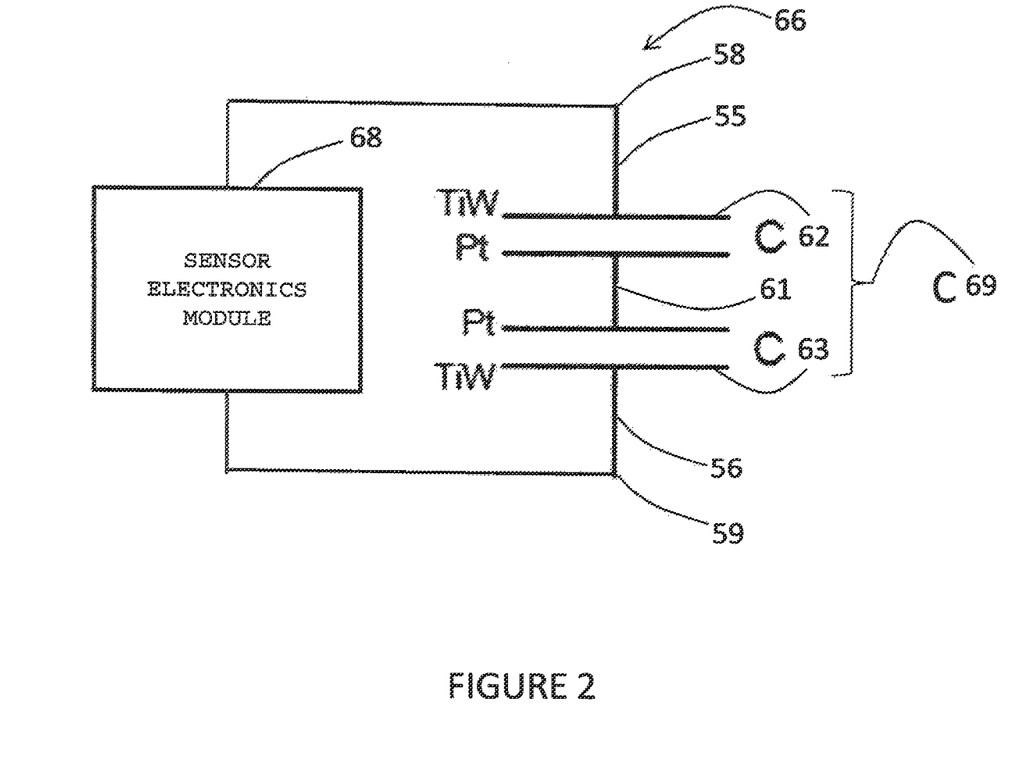
FIG. 2 is a diagram of a basic equivalent circuit of the chemical sensor.

FIG. 2 is a diagram of a schematic 66 of electrical aspects of sensor 51. Connections from a sensor electronics module 68 may be made to pads 58 and 59 of sensor 51. Electronics module 68 may measure a capacitance 69 of the series connected capacitances 62 and 63 ($1/C69=1/C62+1/C63$) to determine a magnitude of a parameter of a fluid being detected by sensor 51. Sensor 51 may need to be calibrated relative to an amount of change of a dielectric constant due to a parameter change of the fluid, and/or to an amount of capacitance representing a certain magnitude of the parameter of the fluid.

Figure 3:
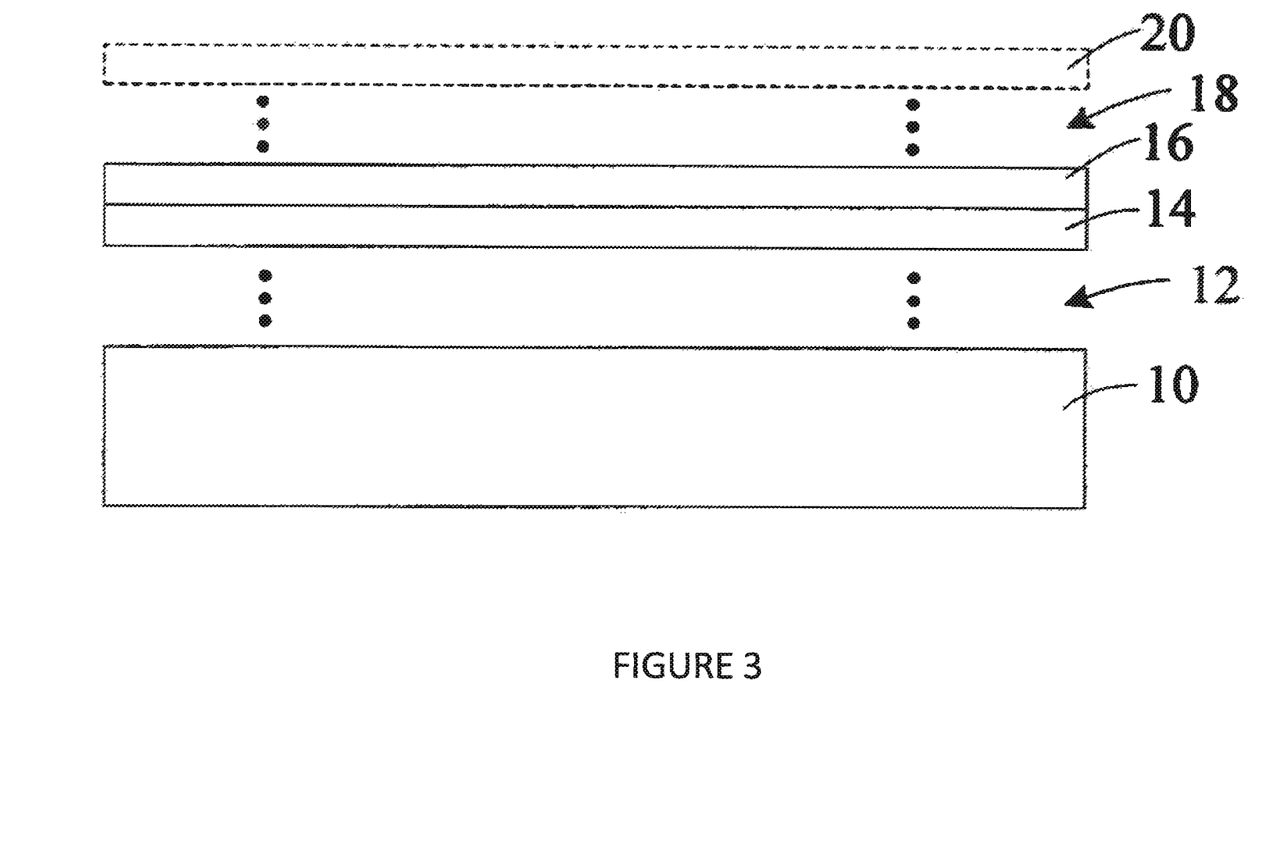
FIG. 3 is a schematic cross-sectional view of an illustrative chemical sensor.

FIG. 3 is a diagram of a substrate 10 and other layers. On substrate 10, a first layer 14 of conductive spheres may be placed, with each conductive sphere contacting another to form an electrically continuous layer that can also be seen in FIGS. 4 and 5. The first layer 14 of conductive spheres 14' may be provided on the substrate 10. Alternatively, there may be one or more intervening layers 12 between the first layer 14 of conductive spheres 14' and the substrate 10. A second layer 16 of conducting spheres 16' may be provided on the first layer 14 of conducting spheres 14'. The second layer 16 of conducting spheres 16' may make electrical contact with the first layer 14 of conducting spheres 14'. Additional layers of conducting spheres may be provided in a similar manner, as desired. Alternatively, or in addition, other layers 18 may be provided above the first layer 14 and the second layer 16, as shown at layers 18 and 20.

It is contemplated that the first layer 14 and the second layer 16 of conductive spheres may be deposited, sometimes without a vacuum system. For example, in some instances, the conductive spheres may be floated in a continuous layer on a liquid surface and directly transferred to a desired surface. One approach for performing this step may be found in T. Wen and S. A. Majetich, ACS Nano, vol. 5, no. 11, 2011, pp. 8868-8876. In some cases, the substrate 10 may be dipped into a solution with suitable conductive spheres and then dried to form the first layer 14 and/or second layer 16. Alternatively, or in addition, the substrate 10 may be coated with a solution with suitable conductive spheres and then dried to form the first layer 14 and/or second layer 16. Alternatively, or in addition, a liquid suspension having the conductive spheres can be ink-jet printed onto the desired surface. Equipment suitable for ink-jet printing a liquid suspension having suitable conductive spheres is available from Microfab Technologies Inc., located in Plano, Tex. Alternatively or in addition, the substrate and/or layers 14 and 16 may be made with 3D printing. Layers 14 and 16, any other layers, may be made with another suitable process.

By choosing the right type of carrying fluid(s), the carrying fluid can evaporate after deposition of the conductive spheres, leaving behind a continuous layer of conductive spheres, sometimes resulting in a monolayer of conductive spheres organized into a single layer. In some instances, the choice of microsphere diameter may be used to control the size and density of the pores between the microspheres. Also, if the spheres are monodisperse (i.e., virtually all of the spheres are the same size), the pore distribution across the layer may be uniform. In some cases, the pore size may be varied across the layer or between layers by changing the size of the spheres, resulting in a non-uniform distribution of pore sizes.

Figure 4:
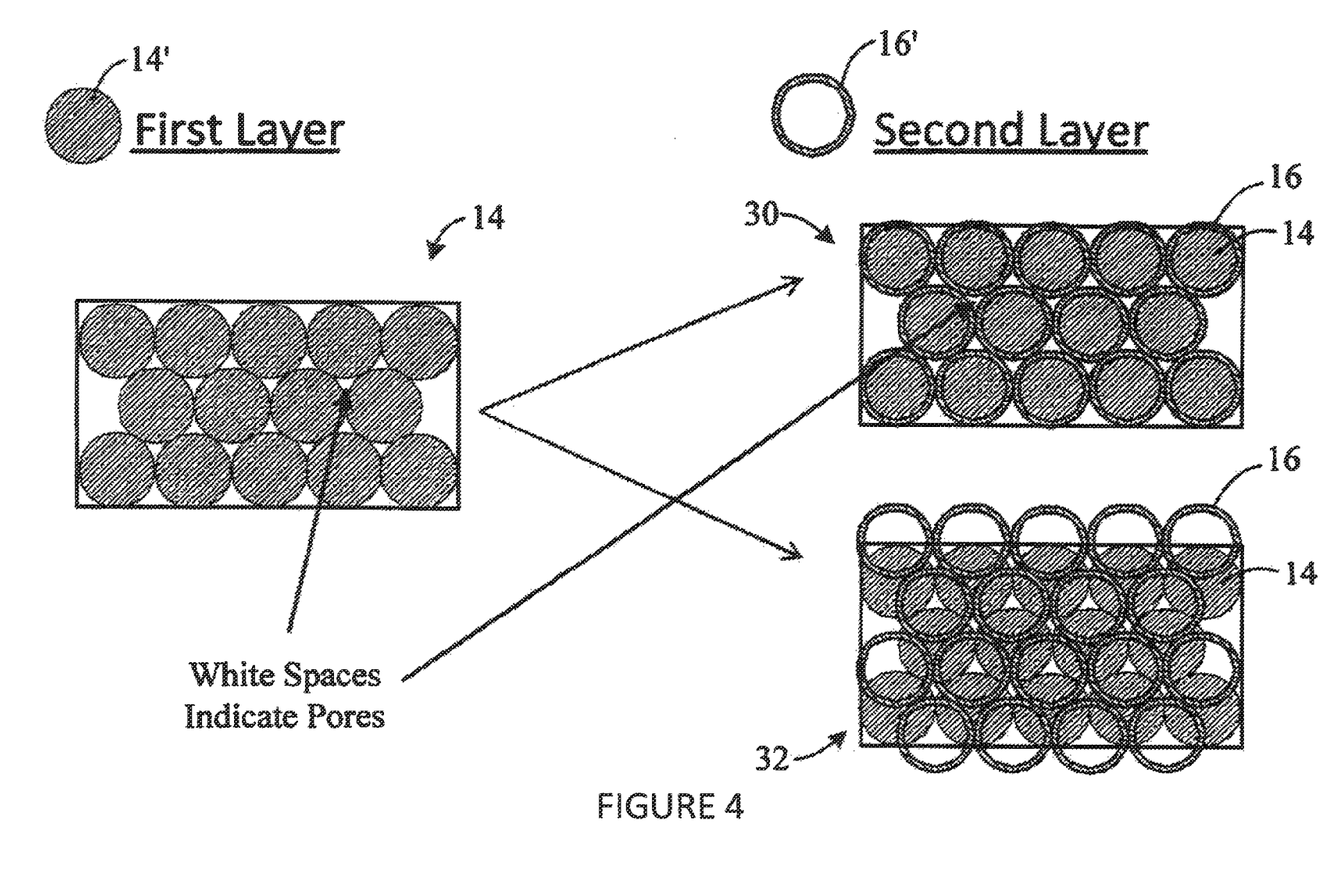
FIG. 4 is a schematic view of an illustrative first layer and second layer of conductive particles.
Figure 5:
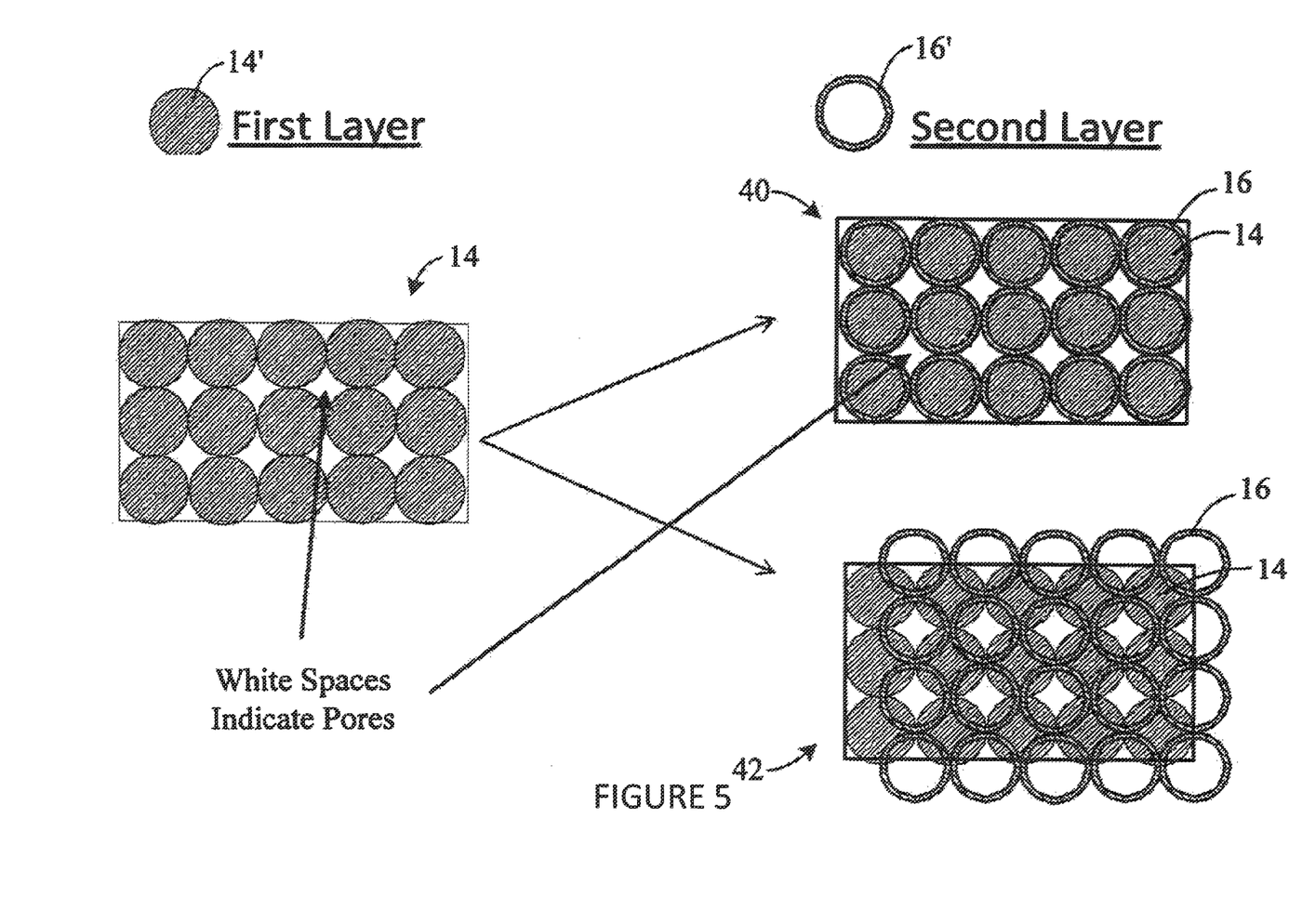
FIG. 5 is a schematic view of another illustrative first layer and second layer of conductive particles.

FIGS. 4 and 5 are diagrams showing a first layer 14 of conductive spheres 14' that may be first deposited. In FIG. 4, each row of the conductive spheres 14' of the first layer 14 is shown offset relative to the adjacent row so that the conductive spheres 14' intermesh with one another. The pores may be formed between the conductive spheres 14'. In FIG. 5, each row of the conductive spheres 14' of the first layer 14 is shown aligned with the adjacent row. Again, the pores are formed between the conductive spheres 14'. In either case, each conductive sphere 14' of the first layer 14 may contact another to form an electrically continuous layer.

The arrangement of the conductive spheres 14' shown in FIG. 5 may generally result in larger pores in the first layer 14 than the arrangement of the conductive spheres 14' shown in FIG. 4. In some instances, the arrangement of conductive spheres 14' in the first layer 14 may not be in a regular pattern as shown in FIG. 4 or FIG. 5, but rather may be arranged in an irregular pattern (not shown). Also, it is contemplated that the conductive spheres 14' of the first layer 14 may be of different diameters, resulting in an irregular pattern. In some instances, the first layer 14 of conductive spheres 14' may produce a monolayer, but this is not required.

In some instances, a second layer 16 of conductive spheres 16' may be deposited on the first layer 14. In FIG. 4, each row of the conductive spheres 16' of the second layer 16 is shown offset relative to the adjacent row so that the conductive spheres 16' intermesh with one another. The pores are formed between the conductive spheres 16'.

In FIG. 5, each row of the conductive spheres 16' of the second layer 16 is shown aligned with the adjacent row. Again, the pores are formed between the conductive spheres 16'. In either case, each conductive sphere 16' of the second layer 16 may contact another to form an electrically continuous layer. The arrangement of the conductive spheres 16' shown in FIG. 5 may result in larger pores in the second layer 16 than the arrangement of the conductive spheres 16' shown in FIG. 4. In some instances, the conductive spheres 16' in the second layer 16 may not be in a regular pattern as shown in FIG. 4 or FIG. 5, but rather may arranged in an irregular pattern. Also, it is contemplated that the conductive spheres 16' of the second layer 16 may be of different diameters, resulting in an irregular pattern. Also, the conductive spheres 16' of the second layer 16 may be of the same or different diameters that the conductive spheres 14' of the first layer. In some instances, the second layer 16 of conductive spheres 16' may produce a monolayer, but this is not required.

FIG. 4 also shows the conductive spheres 16' of the second layer 16 aligned with the conductive spheres 14' of the first layer 14 at arrangement 30, and the conductive spheres 16' of the second layer 16 offset with respect to the conductive spheres 14' of the first layer 14 at arrangement 32. When the conductive spheres 16' of the second layer 16 are aligned with the conductive spheres 14' of the first layer 14, pores may extend vertically (vertical relative to the page) through the first layer 14 and the second layer 16. When the conductive spheres 16' of the second layer 16 are offset with the conductive spheres 14' of the first layer 14, the conductive spheres 14' of the first layer 14 may intermesh with the conductive spheres 16' of the second layer 16, and the pores may have a more tortuous path through the first layer 14 and the second layer 16. In some instances, the conductive spheres 14' of the first layer 14 may electrically connect with conductive spheres 16' of the second layer 16 to form an electrically continuous layer.

FIG. 5 shows the conductive spheres 16' of the second layer 16 aligned with the conductive spheres 14' of the first layer 14 at arrangement 40, and the conductive spheres 16' of the second layer 16 offset with the conductive spheres 14' of the first layer 14 at arrangement 42. When the conductive spheres 16' of the second layer 16 are aligned with the conductive spheres 14' of the first layer 14, pores may extend vertically (vertical relative to the page) through the first layer 14 and the second layer 16. When the conductive spheres 16' of the second layer 16 are offset with the conductive spheres 14' of the first layer 14, the conductive spheres 14' of the first layer 14 may intermesh with the conductive spheres 16' of the second layer 16, and the pores may have a more tortuous path through the first layer 14 and the second layer 16. In some instances, the conductive spheres 14' of the first layer 14 may electrically connect with conductive spheres 16' of the second layer 16 to form an electrically continuous layer.

To recap, a chemical sensor may incorporate a substrate, a first electrode situated on the substrate, a second electrode situated on the substrate, a dielectric layer situated on the first and second electrodes, a third electrode situated on the dielectric layer to form a capacitance between the third electrode and the first and second electrodes. The third electrode may incorporate one or more layers of conductive particles adjacent to one another resulting in pores among the conductive particles. The pores may permit a fluid to pass through the third electrode to the dielectric layer.

The fluid may affect a dielectric constant of the dielectric layer. A magnitude of the capacitance may be proportionally related to the dielectric constant of the dielectric layer.

The capacitance may be indicative of a magnitude of a parameter of the fluid. The fluid may be air and the parameter may be humidity.

Each conductive particle of the one or more layers of conductive particles may have a size or dimension between one nanometer and 2000 microns. The conductive particles may have sizes or dimensions that vary less than ten percent from one another. In certain situations, the sizes, dimensions for the particles may be different than just stated and have other variations relative to one another.

The conductive particles may incorporate a material selected from a group consisting of platinum, gold, palladium, silver, chrome, aluminum, titanium, conductive polymers, and metal oxides.

The dielectric layer may incorporate a polyimide or other appropriate or suitable material.

A size and number of pores may be determined by a size of the conductive particles and a number of layers of the conductive particles, which may be for example, spheres in the third electrode. Determining the size and number of pores may be a control of porosity of the third electrode.

An approach of forming a structure of a chemical sensor, may incorporate forming a plurality of first conductive particles as at least of a part of a first layer of conductive particles, each of the plurality of first conductive particles contacting an adjacent first conductive particle to form a first electrically continuous layer, the plurality of first conductive particles having a shape that creates pores between the plurality of first conductive particles of the first layer; and forming a plurality of second conductive particles secured relative to the first layer as at least as a part of a second layer of conductive particles, each particle of the plurality of second conductive particles contacting an adjacent second conductive particle to form a second electrically continuous layer, and each particle of the plurality of second conductive particles of the second layer contacting an adjacent one of the plurality of first conductive particles, the plurality of second conductive particles having a shape that creates pores between the plurality of second conductive particles of the second layer; and the plurality of first conductive particles and the plurality of the second conductive particles having a shape that creates pores between the first layer and the second layer.

The plurality of first conductive particles and the plurality of the second conductive particles may be formed by a process selected from a group consisting of dip coating, ink-jet printing process, 3D printing, or other suitable process.

The approach may further incorporate forming a dielectric layer having a first side on one or more electrodes. The plurality of first conductive particles and the plurality of the second conductive particles may constitute another electrode situated on a second side of the dielectric layer.

The conductive particles may have a spherical shape.

The one or more electrodes and the other electrode on the first and second sides, respectively, of the dielectric layer may constitute a capacitance. The dielectric layer may have a dielectric constant that can vary upon receipt of a fluid through the other electrode to the second side of the dielectric layer.

A variation of the dielectric constant may be an indication of a magnitude of a parameter of a fluid. The variation may be determined by measuring a corresponding change of the capacitance to indicate the magnitude of the parameter.

A size and number of pores may be determined by the plurality of first conductive particles and the plurality of the second conductive particles having a shape that creates the pores through the first layer and the second layer. Determining the size and number of pores may be a control of porosity of the plurality of first conductive particles and the plurality of the second conductive particles.

The fluid may be air and the parameter may be humidity.

A sensing mechanism may incorporate a substrate, one or more electrodes formed on the substrate, a dielectric formed on the one or more electrodes, and a plurality of first conductive particles secured as another electrode on the dielectric opposite to the one or more electrodes as part of a first layer of conductive particles, each of the plurality of first conductive particles contacting an adjacent first conductive particle to form a first electrically continuous layer, and the plurality of first conductive particles having a shape that creates pores among the plurality of first conductive particles of the first layer.

The sensor may further incorporate a plurality of second conductive particles secured to the first layer, as at least a part of a second layer of conductive particles, each particle of the plurality of second conductive particles contacting an adjacent second conductive particle to form a second electrically continuous layer, and each of the plurality of second conductive particles of the second layer contacting an adjacent one of the plurality of first conductive particles, the plurality of second conductive particles having a shape that creates pores between the plurality of second conductive particles of the second layer, and the plurality of first conductive particles and the plurality of the second conductive particles having a shape that creates pores between the first layer and the second layer. There may be one or more additional layers conductive particles.

Each conductive particle of the plurality of first conductive particles and the plurality of the second conductive particles may be a conductive sphere. Each conductive sphere of the one or more layers of conductive spheres may have a size between one nanometer and 2000 microns. The conductive spheres of the plurality of first conductive particles and the plurality of the second conductive particles may have sizes that vary less than ten percent from one another.

A size and number of pores may be determined by a size of the conductive particles of the plurality of first conductive particles and the plurality of the second conductive particles. Determining the size and number of pores may be a control of porosity of the plurality of first conductive particles and the plurality of the second conductive particles.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. A chemical sensor comprising:
   a substrate;
   a first electrode situated on the substrate;
   a second electrode situated on the substrate;
   a dielectric layer situated on the first and second electrodes; and
   a third electrode situated on the dielectric layer to form a capacitor having a capacitance between the third electrode and the first and second electrodes;
   wherein the third electrode comprises one or more layers of electrically conductive particles adjacent to one another resulting in pores among the electrically conductive particles;
   wherein pores are between a plurality of first electrically conductive particles of a first layer, between a plurality of second electrically conductive particles of a second layer, and between the first layer and the second layer;
   wherein the pores permit a fluid to pass through the third electrode to the dielectric layer.

2. The sensor of claim 1, wherein:
   the fluid can affect a dielectric constant of the dielectric layer;
   a magnitude of the capacitance is proportionally related to the dielectric constant of the dielectric layer; and
   the capacitance indicates a magnitude of a parameter of the fluid.

3. The sensor of claim 2, wherein the fluid is air and the parameter is humidity.

4. The sensor of claim 1, wherein:
   the electrically conductive particles are spheres;
   each electrically conductive sphere of the one or more layers of electrically conductive spheres has a size between one nanometer and 2000 microns; and
   the electrically conductive spheres have sizes that vary less than ten percent from one another.

5. The sensor of claim 1, wherein the electrically conductive particles comprise a material selected from a group consisting of platinum, gold, palladium, silver, chrome, aluminum, titanium, conductive polymers, and metal oxides.

6. The sensor of claim 1, wherein:
   a size and number of pores are determined by one or more items of a group consisting of a size of the electrically conductive particles, a number of layers of the electrically conductive particles in the third electrode, and a number of electrically conductive particles in the layers; and
   determining the size and number of pores is a control of porosity of the third electrode.

7. The sensor of claim 1 wherein the one or more layers of electrically conductive particles adjacent to one another resulting in pores among the electrically conductive particles comprise:
   a plurality of first electrically conductive particles as part of a first layer of electrically conductive particles, each of the plurality of first electrically conductive particles contacting an adjacent first electrically conductive particle to form a first electrically continuous layer; and
   a plurality of second electrically conductive particles as part of a second layer of electrically conductive particles, each electrically conductive particle of the plurality of second electrically conductive particles contacting an adjacent second electrically conductive particle to form a second electrically continuous layer, and each of the plurality of second electrically conductive particles of the second layer contacting and secured to an adjacent one of the plurality of first electrically conductive particles.

8. The sensor of claim 7 wherein the plurality of second electrically conductive particles of the second layer are aligned with respect to the plurality of first electrically conductive particles of the first layer.

9. A method of forming a structure of a chemical sensor, comprising:
   forming a plurality of first electrically conductive particles as at least a part of a first layer of electrically conductive particles, each of the plurality of first electrically conductive particles contacting an adjacent first electrically conductive particle to form a first electrically continuous layer;
   forming a plurality of second electrically conductive particles as part of a second layer of electrically conductive particles, each electrically conductive particle of the plurality of second electrically conductive particles contacting an adjacent second electrically conductive particle to form a second electrically continuous layer, and each electrically conductive particle of the plurality of second electrically conductive particles of the second layer contacting an adjacent one of the plurality of first electrically conductive particles;
   wherein pores are between the plurality of first electrically conductive particles of the first layer, between the plurality of second electrically conductive particles of the second layer, and between the first layer and the second layer;
   forming a dielectric layer having a first side on the first layer of electrically conductive particles; and
   forming one or more electrodes on a second side of the dielectric layer; and
   wherein the plurality of first electrically conductive particles and the plurality of the second electrically conductive particles constitute another electrode situated on the first side of the dielectric layer.

10. The method of claim 9, wherein:
    the one or more electrodes and the other electrode on the first and second sides of the dielectric layer, respectively, constitute a capacitor; and
    the dielectric layer has a dielectric constant that can vary upon receipt of a fluid through the other electrode on the first side of the dielectric layer.

11. The method of claim 10, wherein:
    a variation of the dielectric constant is an indication of a magnitude of a parameter of a fluid; and
    the variation is determined by measuring a corresponding change of a capacitance to indicate the magnitude of the parameter.

12. The method of claim 9, wherein:
    a size and number of the pores are determined by the plurality of first electrically conductive particles and the plurality of the second electrically conductive particles; and
    determining the size and the number of the pores is a control of porosity of the plurality of the first electrically conductive particles and the plurality of the second electrically conductive particles.

13. The method of claim 9, wherein the electrically conductive particles have a spherical shape.

14. The method of claim 9, wherein the plurality of the first electrically conductive particles and the plurality of the second electrically conductive particles are provided by a process selected from a group consisting of dip coating, ink-jet printing process, and 3D printing.

15. The method of claim 9 wherein the plurality of first electrically conductive particles and the plurality of second electrically conductive particles each are in a carrying fluid that evaporates after deposition.

16. A sensor comprising:
a substrate;
one or more electrodes formed on the substrate;
a dielectric formed on the one or more electrodes; and
a plurality of first electrically conductive particles secured as another electrode on the dielectric opposite to the one or more electrodes as part of a first layer of electrically conductive particles, each of the plurality of first electrically conductive particles contacting an adjacent first electrically conductive particle to form a first electrically continuous layer;
a plurality of second electrically conductive particles as part of a second layer of electrically conductive particles, each electrically conductive particle of the plurality of second electrically conductive particles contacting an adjacent second electrically conductive particle to form a second electrically continuous layer, and each of the plurality of second electrically conductive particles of the second layer contacting an adjacent one of the plurality of first electrically conductive particles;
wherein pores are between the plurality of first electrically conductive particles of the first layer, between the plurality of second electrically conductive particles of the second layer, and between the first layer and the second layer.

17. The sensor of claim 16, wherein:
each electrically conductive particle of the plurality of first electrically conductive particles and the plurality of the second electrically conductive particles is an electrically conductive sphere;
a size and number of pores are determined by a size and a number of electrically conductive spheres of the plurality of first electrically conductive particles and the plurality of the second electrically conductive particles; and
determining the size and the number of the pores is a control of porosity of the electrically conductive particles.

18. The sensor of claim 16 wherein the one or more electrodes on the substrate comprise a first electrode situated on the substrate and a second electrode situated on the substrate wherein the dielectric is also between the first and second electrodes.

19. The sensor of claim 16 wherein the plurality of first electrically conductive particles is of a different diameter than the plurality of second electrically conductive particles.

20. The sensor of claim 16 wherein the plurality of second electrically conductive particles of the second layer are offset with respect to the plurality of first electrically conductive particles of the first layer.

* * * * *

UNITED STATES PATENT AND TRADEMARK OFFICE
CERTIFICATE OF CORRECTION

PATENT NO. : 9,933,384 B2
APPLICATION NO. : 15/028110
DATED : April 3, 2018
INVENTOR(S) : Scott Edward Beck It is certified that error appears in the above-identified patent and that said Letters Patent is hereby corrected as shown below:

In the Specification

- Column 1, CROSS-REFERENCE TO RELATED APPLICATIONS, Line 3: "A CHEMICAL SENSOR SYSTEM" should be "A CHEMICAL CAPACITANCE SENSOR"

- Column 2, Line 23: insert --is-- after "there"
- Column 2, Line 53: insert --there-- before "may"

- Column 3, Line 15: "conducting" should be "conductive"
- Column 3, Line 16: "conducting" should be "conductive"
- Column 3, Line 17: "conducting" should be "conductive"
- Column 3, Line 18: "conducting" should be "conductive"
- Column 3, Line 19: "conducting" should be "conductive"
- Column 3, Line 42: insert --or-- before "any"

- Column 4, Line 29: insert --be-- after "may"
- Column 4, Line 34: "that" should be "than"

- Column 6, Line 50: insert --of-- after "layers"

In the Claims

- Column 7, Line 61: insert --,-- after "1"

- Column 8, Line 13: insert --,-- after "7"
- Column 8, Line 62: insert --a-- after "and"

- Column 9, Line 10: insert --,-- after "9"

Signed and Sealed this
Ninth Day of October, 2018

Andrei Iancu
*Director of the United States Patent and Trademark Office*

CERTIFICATE OF CORRECTION (continued)
U.S. Pat. No. 9,933,384 B2

- Column 10, Line 19: insert --,-- after "16"
- Column 10, Line 22: insert --,-- after "substrate"
- Column 10, Line 24: insert --,-- after "16"
- Column 10, Line 27: insert --,-- after "16"